United States Patent [19]

Hradil et al.

[11] 4,246,077
[45] Jan. 20, 1981

[54] NON-CYANIDE BRIGHT SILVER ELECTROPLATING BATH THEREFOR, SILVER COMPOUNDS AND METHOD OF MAKING SILVER COMPOUNDS

[75] Inventors: Edward Hradil; Hana Hradil, both of Warwick; Alfred M. Weisberg, Providence, all of R.I.

[73] Assignee: Technic, Inc., Cranston, R.I.

[21] Appl. No.: 945,894

[22] Filed: Sep. 26, 1978

Related U.S. Application Data

[63] Continuation-in-part of Ser. No. 662,511, Mar. 1, 1976, Pat. No. 4,126,524, which is a continuation-in-part of Ser. No. 557,768, Mar. 12, 1975, abandoned.

[51] Int. Cl.³ .................. C07D 207/06; C07D 207/12; C25D 3/46; C25D 3/64
[52] U.S. Cl. .................................... 204/43 R; 204/44; 204/46 R; 260/326.5 A
[58] Field of Search .................... 204/43 R, 44, 46 R, 204/109; 260/326.5 A

[56] References Cited

U.S. PATENT DOCUMENTS

| | | | |
|---|---|---|---|
| 3,238,112 | 3/1966 | Haslam | 204/46 R X |
| 3,293,157 | 12/1966 | Fackso et al. | 204/46 R |
| 3,362,895 | 1/1968 | Foulke | 204/43 R |

FOREIGN PATENT DOCUMENTS

939720  3/1956  Fed. Rep. of Germany ........ 204/46 R

Primary Examiner—G. L. Kaplan
Attorney, Agent, or Firm—Graham, Geoffrey & Reardon

[57] ABSTRACT

A silver and silver alloy electroplating bath; electrolytic solution; water-soluble silver complex for incorporation therein; and the process for electrodeposition of silver and silver alloys; wherein the electrolytic solution and bath have a pH of at least 6, is free of cyanide, and comprises a water-soluble complex formed from the reaction of a silver salt or compound and an organic complexing agent selected from a pyrrolidine-2,5-dione or a 3-pyrroline-2.5-dione.

30 Claims, 1 Drawing Figure

NON-CYANIDE BRIGHT SILVER ELECTROPLATING BATH THEREFOR, SILVER COMPOUNDS AND METHOD OF MAKING SILVER COMPOUNDS

BACKGROUND OF THE INVENTION

This application is a continuation-in-part of application Ser. No. 662,511 filed Mar. 1, 1976, now U.S. Pat. No. 4,126,524, which is a continuation-in-part of application Ser. No. 557,768 filed Mar. 12, 1975 and now abandoned.

This invention relates to the electrodeposition of silver and silver alloys from non-cyanide electrolytes employing soluble or insoluble anodes.

In the conventional electrolytic silver plating baths, the electrolytes have almost always been limited to cyanide types because of the high stability constant of the complex $K[Ag(CN)_2]$. Conventional potassium silver cyanide plating solutions excel in current efficiency, brightness of the silver and silver alloy deposit, throwing power and speed of electrodeposition.

These features are enhanced by organic and inorganic brighteners or combinations thereof.

A significant shortcoming of the silver cyanide bath is the hydrolysis of cyanide ions ($CN^-$) to form poisonous hydrocyanic acid (HCN). As a consequence, constant care must be taken and efficient ventilation supplied to the area surrounding the bath. Another disadvantage of the silver cyanide electrolytic bath is the presence of the cyanide ions ($CN^-$) near to or directly upon the anode, and especially on an insoluble anode at which the foregoing cyanide ions are liberated together with oxygen to form cyanate ($CNO^-$) ions which react with the water of the bath to yield ammonia and carbon dioxide, the latter forming potassium carbonate; the accumulation of which in the electrolyte necessitates a costly and complicated process to effect its removal.

Additionally, where conventional cyanide silver electrolyte is used, a preliminary silver strike is necessary to secure effective adhesion of the silver or silver alloy to a metal substrate such as brass or copper.

It has been known heretofore to prepare a substantially water-insoluble silver succinimide having a 1:1 molar ratio of silver to succinimide by reaction of one molar equivalent of succinimide with a water-soluble silver salt in a medium having a pH of less than 6. The foregoing product is reported in *Beilstein's Handbuch der Organischen Chemie* Vierte Auflage, Verlag von Julius Springer 1935, Vol. 21, page 371, and while readily isolated, are without utility in the electrodeposition of silver.

Heretofore, most electrolytic solutions for use in non-cyanide silver plating baths have been based on ammonia complexes of silver in combination with a variety of conductivity salts. Illustrative solutions of this type are suggested in U.S. Pat. Nos. 2,504,272; 3,406,107; 3,362,895; and 3,507,758; abstracts of Russian certificates of invention Nos. 138,788, 199,621; 203,423; 212,690; 337,435; Japanese patent publication No. JA 703,9945; and British Pat. No. 1,047,789. The abstracts of Russian Pat. Nos. 185,659; 212,689; 295,824; and 312,892 suggest silver formulations employing amide and amine complexes. None of the foregoing formulations is believed to have found industrial application because the silver complex is unstable during the extended period of time required for stability of the silver complex in a plating bath. The deposits are of poor quality and must be deposited at extremely low current densities.

Thus, if stable, water-soluble, cyanide-free silver complexes capable of producing deposits of silver and silver alloys of good quality by electrodeposition could be developed, while avoiding the pollution, high toxicity and undesired accumulations of potassium carbonate incident to use of conventional cyanide electrolytes; with a concomitant reduction in the number of steps required in the electroplating process, at least in certain instances, such as the elimination of a preliminary silver strike, without adversely affecting the adhesion of the silver deposit secured over brass and copper, a significant advance in the state of the art would be attained.

SUMMARY OF THE INVENTION

It is, accordingly, an object of this invention to provide a non-cyanide silver plating bath that will readily plate a uniform pure silver or silver alloy deposit over a variety of conductive surfaces.

It is an object of the invention to provide a process of electroplating in which, in contrast to conventional techniques, the number of processing steps such as those occasioned by the use of a preliminary silver strike, is reduced.

A further object of the invention is the provision of effective cyanide-free electrolytic solutions and water-soluble cyanide-free silver complexes for use in electrodeposition of silver and silver alloys.

An additional object is the provision of a process for preparing said water-soluble silver complexes.

A still further object involves the formulation of cyanide-free electrolytic baths incorporating, individually or in combination, amine and metallic brighteners and metal salts as alloying components.

It is a particular object of this invention, in addition, to produce bright and semi-bright, including mirror bright, silver and silver alloy electroplates that are equal to or better than presently used cyanide-containing silver plating baths.

It is also an object of the invention to produce mirror bright silver and silver alloy deposits over wide ranges of current densities.

It is an object, as well, of this invention to provide a non-cyanide silver plating electrolyte and bath that is able to produce mirror bright silver deposits without any alloying metals.

Generally, in accordance with the invention, the foregoing, as well as other objects and advantages, are secured by provision of a non-cyanide silver and silver alloy electrolytic solution and electroplating bath incorporating the foregoing solution and containing a water-soluble organic anionic silver complex prepared by reaction of a silver compound and, as a complexing agent, a pyrrolidine-2,5-dione, a 3-pyrroline-2,5-dione, or mixtures thereof. The silver complex is utilized most desirably in the form of its alkali metal or ammonium salt. Electrodeposition of silver or silver alloy on the cathode of the electroplating bath takes place in the presence, optionally, of conductivity salts; brighteners and alloying components.

The foregoing and other objects and advantages of the invention will be evident from the description that appears hereinafter.

DETAILED DESCRIPTION OF THE INVENTION

The electrolytic solutions for use, particularly, in an electroplating bath, in accordance with the invention, are those having a pH of at least 6, and more expressly, from 6 to 14, and free of cyanide, incorporating a reaction product of a water-soluble silver complex of a pyrrolidine-2,5-dione or a 3-pyrroline-2-5-dione or a substituted derivative thereof. These reaction products or complexes are prepared by reacting one gram mole equivalent of a silver compound with at least two gram mole equivalents of a pyrrolidine-2,5-dione or two gram mole equivalents of a 3-pyrroline-2,5-dione or their derivatives as further characterized hereinafter. The reaction occurs in the presence of an at least stoichiometric concentration of an inorganic base or similar acid binding agent.

The five member heterocyclic ring compounds, pyrrolidine-2,5-diones (I) and 3-pyrrolidine-2,5-diones (II), used to complex silver ions in accordance with the invention are represented by the following general formulae:

where, in formula I, R is hydrogen (—H), alkyl or alkoxy; and, formula II, R' is hydrogen or alkyl, the foregoing alkyl and alkoxy moieties preferably do not exceed four carbon atoms in size, that is, they contain from one to four carbon atoms, each of the moieties represented by each of R and R' being the same or different. Typical and preferred compounds coming within the group or groups represented by the foregoing formulae I and II for providing an electrolyte of silver in complexes with organic compounds such as succinimide, or pyrrolidine-2, 5-dione and maleimide, or 3-pyrroline-2,5-dione.

Useful and commercially available imides, in addition, include 3,3-dimethyl pyrrolidine-2, 5-dione (2,2-dimethyl succinimide) and 3-methyl 3-ethyl pyrrolidine-2,5-dione (2-methyl 2-ethyl succinimide). Further illustrative of the heterocyclic imides suitable for forming silver imide complexes while maintaining a solubility in water adequate to keep silver in solution in an electrolytic bath in accordance with the practice provided herein, are 3-methyl-3-ethyl pyrrolidine-2, 5-dione (2-methyl-2-ethyl succinimide), 3-methyl pyrrolidine-2,5-dione (2-methyl succinimide), 3-ethyl pyrrolidine-2,5-dione (2-ethyl succinimide), 3,3,4,4-tetramethyl pyrrolidine -2,5-dione (1,1,2,2, -tetramethyl succinimide), 3,3,4-trimethyl pyrrolidine-2,5-dione (1,1,2-trimethyl succinimide), 3-butyl pyrrolidine-2,5-dione (2-butyl succinimide), 3-ethyl-3-pyrroline-2,5-dione (2-ethyl maleimide), 3-methyl-4-ethyl-3 pyrroline-2,5-dione (1-methyl-2-ethyl maleimide), 3-butyl-3 pyrroline-2,5-dione (2-butyl maleimide), and 3-methyl-4-ethyl-3-pyrroline-2,5-dione (1-methyl-2-ethyl maleimide).

The silver compounds or complexes prepared in accordance with the invention are alkali metal or ammonium silver diimides or the general formulae:

wherein M is an alkali metal cation or ammonium ($NH_4^+$); and R and R' is, in each instance, as defined hereinabove.

Illustrative of these products are potassium silver disuccinimide, ammonium silver disuccinimide, potassium silver dimaleimide, ammonium silver dimaleimide, sodium silver disuccinimide, potassium silver di (3,3-dimethyl pyrrolidine 2,5-dione), and ammonium silver di(3-methyl-4-ethyl pyrrolidine 2,5-dione).

Figure 1:
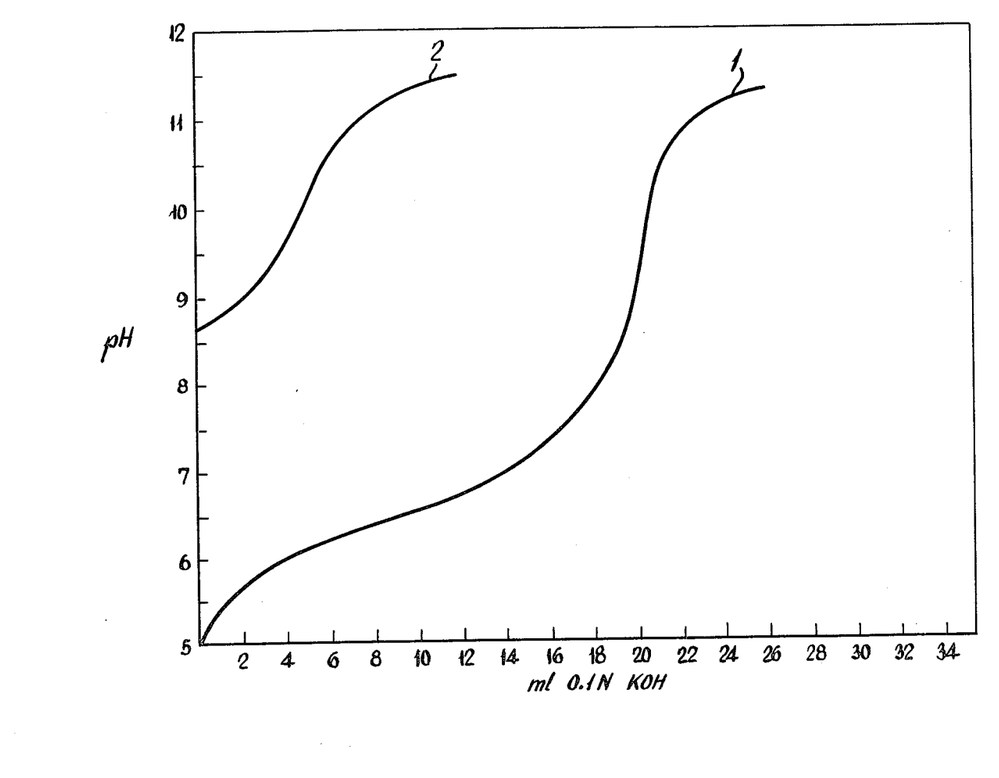
The drawing illustrates different methods of producing the novel silver complexes according to the invention.

Illustrative of the process, in accordance with the invention, is that in at least 2 gram moles of pyrrolidine-2,5-dione (succinimide) is reacted with one gram mole of a water-soluble, silver salt, such as silver nitrate, or one half gram mole of a water-insoluble silver salt, such as silver carbonate, in the presence of an approximately stoichiometric amount of an inorganic base such as potassium hydroxide. The formation of the desired silver imide compound is illustrated in the following equation:

The production of the foregoing alkali metal silver succinimide complex wherein 1 mole of silver salt is reacted with 2 moles of succinimide is shown in the accompanying drawing wherein the stepwise formation of the foregoing complex is reflected in curve (1) by the pH of the reaction mixture upon addition thereto of 0.1 N potassium hydroxide measured in milliliters using the titrimetric method described by G. Schwarzenbach, *Die Komplexometrische Titration* (1955) F. Enke Verlag.

Curve 2 of the drawing reflects, using the foregoing titrimetric method of determination of Schwarzenbach et al., the conversion of the substantially water-insoluble silver-pyrrolidine-2,5-dione complex [formed by reaction of equimolar (1:1) proportions of silver nitrate and succinimide] to the water-soluble silver imide complex incorporating one mole of silver for each two moles of imide as shown in Equation (1) hereinabove. The conversion to the complex of Equation (1) is illustrated in the following Equation (21):

Other inorganic water-soluble and water-insoluble silver salts and compounds; and, indeed, other alkali metal, and ammonium containing bases, in addition to potassium hydroxide, such as sodium hydroxide or ammonium hydroxide, lithium hydroxide, rubidium hydroxide or cesium hydroxide, well known to those skilled in the art are used in preparing the silver imide complexes according to the invention.

The reaction includes sufficient base to assure a pH of 6 to 14, as indicated above, and preferably 8 to 11. While the silver imide complex formed can be readily isolated by standard means and utilized as such in the electrolytic solution of the invention, it is most convenient to use the water-soluble complex in the reaction product mixture.

It has been found, in accordance with the present invention, that the foregoing non-cyanide silver complexes have particular application in electrodeposition of silver and silver alloys, and most desirably where alloys are employed, with gold, antimony, palladium and related metals, preferably, in a range of up to 5 percent by weight of the silver content.

The process of electrodeposition, in accordance with the invention, is effected by passing an electric current to a cathode to be plated through an electroplating bath composed of an aqueous solution having a pH of at least 6 or, 6 to 14 inclusive as noted hereinabove; preferably from 8 to 11 inclusive, and most desirably 8.5 to 10; with an optimum pH of about 8–9, and incorporating a water-soluble silver complex, as described herein, and including, for the purpose of securing mirror-bright silver deposits, an amine, including alkyl, alkylene, alkylol, alkanol, or alkyaryl amines and alkylene polyamines and polyalkylene polyamines, embraced by the general formula:

or the cross-linked derivatives thereof, wherein $R^2$ is hydrogen (—H), amino (—$NH_2$) or phenyl; each of $R^3$ and $R^4$ is hydrogen, or an alkyl, aminoalkyl, or hydroxyalkyl, radical, or a moiety of the general formula:

and wherein; with reference to $R^3$ and $R^4$ in the foregoing formulae IV and V, the alkyl portion of any of the recited radicals contains from 2 to 6 carbon atoms, and where incorporating an amino or hydroxy substituent, said substituent is present in the 2-C or 3-C position of the alkyl radical and is preferably 2-aminoethyl (—$CH_2CH_2$ $NH_2$) or 2-hydroxyethyl (—$CH_2CH_2OH$) respectively; and where the foregoing moiety is a terminal radical, in each instance of its occurrence as $R^3$ or $R^4$, each of $R^3$ and $R^4$ is one of the recited substituents other than the moiety itself; m has a value of 1 to 6, and preferably 1 to 3; each of x and y has a value of 1 to 18 and further the sum of x and y have a value sufficient to afford a polyalkylene polyamine having a molecular weight of up to 60,000 and preferably 60 to 2000. The term "phenyl" as employed with respect to $R^2$ hereinabove is intended to encompass unsubstituted or substituted phenyl moieties, provided in the latter instance, the result does not unduly or materially affect the brightener properties of the amine in which said substituted phenyl radical is incorporated.

The foregoing amines include the following amines, imines, polyamines and polyimines useful as potent and effective brighteners in the non-cyanide silver plating baths of the invention:

wherein $R^5$ is $NH_2$ or —H; $R^2$ is as defined hereinabove; and n is an integer of from 2 to 6; and, as noted, amines of the foregoing general formula IV appearing hereinabove; for example, as indicated, polyethylene imine or polypropylene imine, having a molecular weight of from 60 to 60,000. These compounds are commercially available as polyimines of various molecular weights from 60 to 60,000 from the Dow Chemical Company, Midland, Mich.

The foregoing alkylene or polyalkylene polyamines are intended, as these terms are employed herein, to embrace unsubstituted or substituted compounds provided that the substituents do not unduly interfere with the practice of the invention as otherwise characterized herein. Such substituents include polyalkylene polyamines containing at least one or more secondary or tertiary amine groups. The most active and normally preferred of the amines and polyamine or polyimines are ethylene diamine, diethylene triamine, triethylene tetramine and benzyl amine.

Illustrative of the polyalkylene polyamines to be used as brighteners for non-cyanide silver plating baths herein are: Polyethyleneimine 3 (PEI-3), Polyethyleneimine 6 (PEI-6), Polyethyleneimine 12 (PEI-12), Polyethyleneimine 18 (PEI-18), Polyethyleneimine 600 (PEI-600). The foregoing polyalkyleneimines are marketed by the Dow Chemical Company under the indicated designations.

Further illustrative of the amines for use in the practice of the invention are ethylamine, propylamine, propylenediamine, tetraethylenepentamine, pentaethylenehexamine, imino-bis-propylamine, dimethyl amino propylamine and diethylpropylenediamine. The foregoing amines can be used in the non-cyanide silver plating formulations based on silver complexes as single or individual compounds or in conjunction or combination with one another.

Accordingly, the non-cyanide and, if desired, mirror bright, silver and silver alloy, electrolytic solutions and plating baths of the present invention incorporate the following components: (1) a water-soluble silver complex of a pyrrolidine-2,5-dione or 3-pyrroline-2,5-dione or a substituted derivative thereof; (2) an alkali metal or ammonium hydroxide or other acid binding base; (3) where mirror bright plating is desired, an amine as aforesaid; and additionally, and optionally, the following: (4) secondary or alternative metallic brighteners, (5) one or more conductivity salts and (6) alloying metal salts.

Among the metal salts included in the electroplating bath are copper, cadmium, gold, palladium and antimony. Gold, palladium and antimony are used as hardening or coloring components for improving the properties of silver deposits, particularly for application in certain specialized industrial or jewelry application.

Copper and cadmium salts provide excellent metallic brighteners as well as alloying metals in the non-cyanide silver baths of the invention. Cadmium or copper compounds can be employed alone, in conjuction with each other, or as secondary brighteners in conjunction with the amine brighteners described elsewhere herein.

During the electrolysis of the non-cyanide silver or silver alloy plating bath, the silver is removed from the complex, and the liberated organic complexing agents reacts with silver from the silver anode. Where insoluble anodes are employed, the liberated organic complexing agent reacts with water soluble or water insoluble silver replenishing salt.

The mole ratio of silver ions to complexing agent in the silver imide complex is 1 to 2 respectively; and the silver free complexing agent can be present up to saturation. An excess of free complexing agent, that is, for example, succinimide or maleimide, unreacted with silver, is employed preferably in the plating bath in order to maintain the solubility of the silver anodes and to reduce the concentration of free silver ions ($Ag^+$) in the electrolyte.

A variety of organic and inorganic salts or acids are, as indicated, desirably employed to enhance, optionally, the electrical conductivity of the non-cyanide silver plating bath of the invention. These components, referred to herein interchangeably as conductivity salts, for convenience while embracing the organic acids that are also effective in improving electrical conductivity of the bath as well, encompass, for example, those containing as the anionic constituents, $F^-$, $CO_3^{--}$, $PO_4^{---}$, $HPO_4^{--}$, $SO_3^{--}$, $SO_4^{--}$, $NH_2SO_3^-$, $NO_2^-$, $OH^-$, $NO_3^-$, and mono, di, or tricarboxylates of saturated or unsaturated aliphatic acids and the substituted or unsubstituted derivatives thereof, provided that the substituents do not otherwise interfere with the activity of the bath and the practice of the invention as described herein. Illustrative of these substituents are the hydroxy and amino substituted carboxylates. Further illustrative of these carboxylates are citrate, acetate, maleate, succinate, malate and hydroxyacetate. The cations employed with the foregoing anions are the alkali metals and most desirably potassium, or ammonium. The use of sodium is less preferred.

The concentration of conductivity salts, which forms water-soluble silver salts is not critical. The concentration of conductivity salts which form insoluble silver salts may be narrowly critical but becomes so only at the point where they interfere with the solubilization of the silver at the anode during the electroplating process.

Conventional nonionic or anionic wetting agents or combinations thereof are conveniently and often desirably included in the electroplating baths of the present invention, as well. These surfactants do not exceed 0.01 percent to 0.5 percent by weight of the bath solution.

The electroplating process of the invention is carried out preferably at a temperature of 20° C. to 40° C.

The ranges in proportions of the components of the electrolytic solutions or treatment or plating baths of the invention that are operative, and include preferred compositions, contents and ranges for bright silver plating baths in accordance with the present invention appear in Table I as follows:

TABLE I

| Component | Concentration |
|---|---|
| Silver as complex (e.g. as succinimide complex). | 5 grams to 100 grams per liter. |
| Complexing agent (e.g. succinimide or maleimide (or their derivatives). | 10 grams per liter to saturation. |
| Conductivity salts | 0 to 600 grams, and preferably from 0.1 to 300 grams, per liter. |
| Primary amine brightener; secondary inorganic metallic brighteners; or combinations of the foregoing. | 0, or preferably to secure a mirror bright deposit, 0.001 gram. to 50 grams per liter of either; or, in combination. |
| Alloying metal | .01 to 50 grams per liter |
| Base (alkali metal hydroxide or ammonium hydroxide) | 5 grams to 200 grams per liter, and enough in any event to secure the pH recited in this Table I |
| pH | 6.0 to 14 |
| Water | to 1 liter. |

The concentration of alloying metal present or combinations thereof including that where cadmium or copper are present as secondary brighteners are, when expressed as the cations, $Cu^+$, $Cu^{++}$, $Cd^{++}$, $Au^+$, $Au^{+++}$, $Pd^{++}$ or $Sb^{+++}$, within the range of 0.001 gram to 50 grams per liter; with a preferred range of 0.1 gram to 40 grams per liter.

The non-cyanide silver and silver alloy plating bath operates successfully at temperatures between 20°–40° C. (68° F. to 103° F. or 104° F.); a cathodic current density of between 0.1 to 3 A per square decimeter (dm); an anodic current density of 0.1 to 3 A/dm$^{-2}$ (1 to 30 ASF); a cathode area to anode area ratio of not less than 1:1, respectively, while extremely high ratios, respectively, of 1:10 and more are advantageously employed; a cathode current efficiency, regardless of anodes used, of 90 to 100%; and an anode current efficiency in the case of soluble silver anodes of 90 to 100%.

The following examples are further illustrative of the invention.

EXAMPLE 1

This example illustrates the preparation of potassium silver disuccinimide in accordance with the invention.

Freshly precipitated silver hydroxide produced from 0.1 mole of silver nitrate is dispersed in 300 mls of distilled water. To the dispersion is added 17.0 gm of succinimide (0.2 mole) and 5.6 gm of potassium hydroxide (0.1 mole). The mixture is vigorously agitated to yield a clear solution having a pH of 8.5. The solution is filtered and concentrated to a small volume. A white solid separates and is isolated by filtration. The solid product, potassium silver disuccinimide, is washed several times with small amounts of ethyl alcohol and then dried in vacuum for 48 hrs. at 60° C. and analyzed.

| ELEMENTAL ANALYSIS | | |
|---|---|---|
| Element | Theory | Actual |
| Ag | 31.44% | 30.42% |
| C | 28.00% | 26.23% |
| H | 2.35% | 2.56% |
| K | 11.39% | 12.55% |
| N | 8.16% | 8.10% |
| O | 18.64% | 20.14% |

The potassium silver disuccinimide complex is soluble in water to yield an aqueous solution capable of conducting an electric current.

EXAMPLE 2

This example illustrates the preparation of ammonium silver dimaleimide.

Freshly precipitated silver carbonate (0.05 mole) is dispersed in 300 mls of distilled water. To the dispersion was added maleimide (0.2 mole) and ammonium hydroxide (0.2 mole). The mixture was vigorously agitated to yield a clear solution having a pH of 8.5. The solution was filtered and concentrated to a small volume. The white solid was crystallized out and was isolated by filtration. The solid was washed several times with small amounts of ethyl alcohol and then dried in vacuum for 48 hrs. at 60° C.

EXAMPLE 3

This example illustrates the use of an aqueous, non-cyanide, potassium silver disuccinimide-containing electroplating bath in a silver plating operation.

An aqueous non-cyanide silver electroplating bath was prepared containing silver as pyrrolidine-2,5-dione complex in amount of 22.5 grams per liter. The pH of the bath was adjusted to 8.5 with KOH. The electrolyte containing the complex, potassium silver disuccinimide, was moderately agitated at a temperature of 25° C. (77° F.). A brass plate, 1"×1", was plated for 10 minutes at 1 A.dm$^{-2}$(10 ASF). The resulting deposition was semi-bright and stress-free.

During the electrolysis of the non-cyanide silver or silver alloy plating bath, the silver is removed from the complex, and the liberated organic complexing agent, pyrrolidine-2,5-dione (succinimide) reacts with silver from the silver anode.

EXAMPLE 4

This example is similar to Example 3, but employs a conductivity salt.

An aqueous non-cyanide silver electroplating bath was prepared as follows:

| | |
|---|---|
| Ag as pyrrolidine 2,5-dione complex (Potassium silver disuccinimide) | 22.5 grams per liter |
| Pyrrolidine 2,5-dione | 37.0 grams per liter |
| Potassium fluoride | 37.0 grams per liter |

The pH was adjusted with potassium hydroxide to pH 10. The electrolyte was moderately agitated at temperature of 25° C. (77° F.). A sample was plated at 1 A.dm$^{-2}$ (10 ASF) for 10 minutes. The resulting deposit was semi-bright to bright and stress-free.

EXAMPLE 5

This example employs a procedure similar to that of Example 4, but substitutes a different conductivity salt.

An aqueous non-cyanide silver electroplating bath was prepared as follows:

| | |
|---|---|
| Ag as 3-pyrroline-2,5-dione complex (Potassium silver dimaleimide) | 22.5 grams per liter |
| 3-pyrroline 2,5-dione | 11.5 grams per liter |
| Potassium sulfate | 45.0 grams per liter |

The pH was adjusted with potassium hydroxide to 8.5. The electrolyte was moderately agitated. A sample was plated at a temperature of 25° C. (77° F.) for 19 minutes at 1 A.dm (10 ASF). The resulting deposit was semi-bright to bright and stress-free.

EXAMPLE 6

This example discloses a plating bath using potassium silver disuccinimide electrolyte with still other bath components.

An aqueous non-cyanide silver electroplating bath was prepared as follows:

| | |
|---|---|
| Ag as succinimide complex (Potassium silver disuccinimide) | 30.0 grams per liter |
| Succinimide | 11.5 grams per liter |
| Potassium nitrite | 37.0 grams per liter |

The pH was adjusted with potassium hydroxide to 9. The electrolyte was moderately agitated at a temperature of 25° C. (77° F.). A sample was plated for 10 minutes at 1.5 A.dm$^{-2}$ (15 ASF). The deposit was semi-bright to bright and stress-free.

EXAMPLE 7

This example illustrates another electroplating bath in accordance with the invention for producing semi-bright plated articles.

An aqueous non-cyanide silver electroplating bath was prepared as follows:

| | |
|---|---|
| Potassium silver disuccinimide | 36 grams per liter |
| Succinimide | 55 grams per liter |
| Potassium nitrate | 50 grams per liter |

Potassium hydroxide was used to adjust the pH to 9.5. A sample was plated at a temperature of 30° C. (86° F.) and current density 1 A.dm$^{-2}$ (10 ASF) for 10 minutes. The resulting deposit was uniformly semi-bright to bright.

EXAMPLE 8

This example illustrates a non-cyanide silver electroplating bath containing an amine brightener.

An aqueous non-cyanide silver electroplating bath was prepared as follows:

| | |
|---|---|
| Ag as succinimide complex (Sodium silver disuccinimide) | 22.5 grams per liter |
| Succinimide | 11.5 grams per liter |
| Polyethylenimine-12 | 0.2 grams per liter |

The pH was adjusted with sodium hydroxide to 6.5. A sample was plated for 10 minutes at 0.5 A.dm$^{-2}$ (5 ASF). A bright deposit was obtained with very slight blue hue.

EXAMPLE 9

This example illustrates a silver electroplating bath containing another amine brightener.

The bath was prepared as follows:

| | |
|---|---|
| Ag as succinimide complex (Potassium silver disuccinimide) | 22.5 grams per liter |
| Succinimide | 22.5 grams per liter |
| Potassium nitrite | 20.0 grams per liter |
| Ethylene diamine | 2 milliliters per liter |

The pH was adjusted to a pH of 9.5 with potassium hydroxide. The electrolyte was moderately agitated at a temperature of 25° C. (77° F.). A sample was plated for 10 minutes at 1.5 A/dm$^{-2}$ (15 ASF). The resulting deposit was mirror-bright and stress-free.

EXAMPLE 10

This example illustrates a further non-cyanide electroplating bath incorporating an amine brightener and wetting agent in accordance with the invention.

An aqueous non-cyanide silver electroplating bath was prepared as follows:

| | |
|---|---|
| Ag as succinimide complex (Potassium silver disuccinimide) | 22.5 grams per liter |
| Succinimide | 22.5 grams per liter |
| Triethylenetetramine | 0.1 gram per liter |
| Polyethylene glycol - 1500 | 1.0 gram per liter |

The pH was adjusted to 9 with potassium hydroxide. The electrolyte was moderately agitated at a temperature of 30° C. (86° F.). A sample was plated 10 minutes at 1 A.dm$^{-2}$ (10 ASF). The resulting deposit was bright and stress-free.

EXAMPLE 11

This example illustrates an aqueous silver electroplating bath in accordance with the invention.

An aqueous non-cyanide silver electroplating bath was prepared as follows:

| | |
|---|---|
| Ag as succinimide complex (Potassium silver disuccinimide) | 22.5 grams per liter |
| Succinimide | 22.5 grams per liter |
| Diethylenetriamine | 5 milliliters per liter |
| Wetting Agent FC-170 | 1 grams per liter |

The pH was adjusted with potassium hydroxide to 11. The electrolyte was moderately agitated at a temperature of 25° C. (77° F.). A sample was plated 10 minutes at 1 A.dm$^{-2}$ (10 ASF). Resulting deposit was bright and stress-free.

The following examples 12 to 23 further illustrate silver electrodeposition solutions and plating operations in accordance with the invention:

EXAMPLE 12

An aqueous non-cyanide silver electroplating bath was prepared as follows:

| | |
|---|---|
| Ag as succinimide complex (Potassium silver disuccinimide) | 22.5 grams per liter |
| Succinimide | 11.5 grams per liter |
| Potassium nitrate | 7.5 grams per liter |
| Triethylene tetramine | 0.5 milliliters per liter |

The pH was adjusted with potassium hydroxide to 8.5. The electrolyte was moderately agitated at a temperature of 25° C. (77° F.). Sample was plated 10 minutes at 1 A.dm$^{-2}$ (10 ASF). Resulting deposit was mirror bright and stress-free.

EXAMPLE 13

An aqueous non-cyanide silver electroplating bath was prepared as follows:

| | |
|---|---|
| Ag as succinimide complex (Potassium silver disuccinimide) | 22.5 grams per liter |
| Succinimide | 11.5 grams per liter |
| Polyethyleneimine - 18 | 0.4 grams per liter |
| Polyethylene glycol - 6000 (wetting agent) | 0.15 grams per liter |

The pH was adjusted with potassium hydroxide to 8.5. The electrolyte was moderately agitated at a temperature of 25° C. (77° F.). Sample was plated 10 minutes at 1.5 A.dm$^{-2}$ (15 ASF). Resulting deposit was mirror-bright and stress free.

EXAMPLE 14

An aqueous non-cyanide silver electroplating bath was prepared as follows:

| | |
|---|---|
| Ag as succinimide complex (Sodium silver disuccinimide) | 22.5 grams per liter |
| Succinimide | 11.5 grams per liter |
| Polyethyleneimine - 12 | 0.1 grams per liter |

The pH was adjusted with sodium hydroxide to 6.5. Sample was plated 10 minutes at 0.5 A.dm$^{-2}$ (5 ASF) under same conditions as in Examples 12 and 13. Bright deposit was obtained with very slight blue hue.

EXAMPLE 15

An aqueous non-cyanide silver electroplating bath was prepared as follows:

| | |
|---|---|
| Ag as succinimide complex (Potassium silver disuccinimide) | 30 grams per liter |
| Succinimide | 11.5 grams per liter |
| Potassium nitrite | 37 grams per liter |
| Ethylene diamine | 2 milliliters per liter |

The pH was adjusted with potassium hydroxide to 9. The electrolyte was moderately agitated at a temperature of 25° C. (77° F.). Sample was plated 10 minutes at 1.5 A.dm$^{-2}$ (15 ASF). Deposit was mirror-bright and stress-free.

EXAMPLE 16

An aqueous non-cyanide silver electroplating bath was prepared as follows:

| | |
|---|---|
| Ag as succinimide complex | 22.5 grams per liter |

| | |
|---|---|
| (Potassium silver disuccinimide) | |
| Succinimide | 37 grams per liter |
| Potassium fluoride | 37 grams per liter |
| 1.6-hexanediamine | 4 milliliters per liter |

The pH was adjusted with potassium hydroxide to pH 10. The electrolyte was moderately agitated at temperature of 25° C. (77° F.). Sample was plated at 1 A.dm$^{-2}$ (10 ASF) for 10 minutes. Resulting deposit was bright and stress-free.

EXAMPLE 17

An aqueous non-cyanide silver electroplating bath was prepared as follows:

| | |
|---|---|
| Ag as succinimide complex | 37 grams per liter |
| (Potassium silver disuccinimide) | |
| Succinimide | 22.5 grams per liter |
| Wetting agent FC-95 | 0.01 gram per liter |
| Triethylenetetramine | 0.8 milliliter per liter |

The pH was adjusted to 9 with potassium hydroxide. The electrolyte was moderately agitated at temperature 25° C. (77°). Sample was plated at 0.7 A.dm$^{-2}$ (7 ASF) for 20 minutes. Deposit was mirror-bright and stress-free.

EXAMPLE 18

An aqueous non-cyanide silver electroplating bath was prepared as follows:

| | |
|---|---|
| Ag as succinimide complex | 22.5 grams per liter |
| (Potassium silver disuccinimide) | |
| Succinimide | 11.5 grams per liter |
| Potassium sulfate | 45 grams per liter |
| Tetraethylene pentamine | 0.4 gram per liter |

The pH was adjusted with potassium hydroxide to 8.5. The electrolyte was moderately agitated. Sample was plated at temperature 25° C. (77° F.) for 10 minutes at 1 A.dm$^{-2}$ (10 ASF). Resulting deposit was mirror-bright and stress-free.

EXAMPLE 19

An aqueous non-cyanide silver electroplating bath was prepared as follows:

| | |
|---|---|
| Ag as succinimide complex | 22.5 grams per liter |
| (Potassium silver disuccinimide) | |
| Succinimide | 11.5 grams per liter |
| Polyethyleneimine - 18 | 0.5 gram per liter |
| Ethylenediamine | 2 milliliters per liter |

The pH was adjusted to 10 with KOH. The electrolyte was moderately agitated. Sample was plated at temperature 25° C. (77° F.) for 10 minutes at 1 A.dm$^{-2}$ (10 ASF). Resulting deposit was mirror-bright and stress-free.

EXAMPLE 20

An aqueous non-cyanide silver electroplating bath was prepared as follows

| | |
|---|---|
| Potassium silver disuccinimide | 36 grams per liter |
| Succinimide | 55 grams per liter |
| Potassium nitrate | 50 grams per liter |
| Polyethylene glycol - 6000 | 0.5 grams per liter |

Potassium hydroxide was used to adjust the pH to 9.5. Sample was plated at temperature of 30° C. (86° F.) and current density 1A.dm$^{-2}$ (10 ASF) for 10 minutes. The resulting deposit was uniformly semi-bright to bright.

Examples 21 through 35 illustrate silver electroplating baths and products incorporating amine and metallic brighteners and alloying metals in accordance with the present invention.

EXAMPLE 21

| | |
|---|---|
| Ag as silver succinimide complex | 22.5 grams per liter |
| (Potassium silver disuccinimide) | |
| Cu as copper succinimide complex | 1.5 grams per liter |
| Succinimide | 25.0 grams per liter |
| pH adjusted with potassium hydroxide to 9.0 | |
| Temperature | 25° C. (77° F.) |
| Current density | 0.8A . dm$^{-2}$ (8 ASF) |
| Plating time | 10 minutes |
| Deposit | 98% ag, 2% Cu-mirror bright |
| Current efficiency | 97% |

EXAMPLE 22

| | |
|---|---|
| Ag as silver succinimide complex | 23.0 grams per liter |
| (Potassium silver disuccinimide) | |
| Cu$^{++}$ as copper acetate | 1.0 grams per liter |
| Succinimide | 70.0 grams per liter |
| pH adjusted with potassium hydroxide to 8.5 | |
| Temperature | 25° C. (77° F.) |
| Current density | 1.0 A . dm$^{-2}$ (10 ASF) |
| Plating time | 10 minutes |
| Deposit | 97% Ag, 3% Cu-mirror-bright |
| Current efficiency | 96% |

EXAMPLE 23

| | |
|---|---|
| Ag as silver succinimide complex | 23.0 grams per liter |
| (Potassium silver disuccinimide) | |
| Cu$^{++}$ as Cu(NO$_3$)$_2$ . 3H$_2$O | 1.5 grams per liter |
| Succinimide | 80.0 grams per liter |
| Potassium nitrite | 40.0 grams per liter |
| Ethylene diamine | 2 milliliters per liter |
| pH adjusted with potassium hydroxide to 8.5 | |
| Temperature | 25° C. (77° F.) |
| Current density | 1A . dm$^{-2}$ (10 ASF) |
| Plating time | 10 minutes |
| Deposit | 97% Ag, 3% Cu-mirror-bright |
| Current efficiency | 97% |

EXAMPLE 24

| | |
|---|---|
| Ag as silver succinimide complex | 23.0 grams per liter |
| (Potassium silver disuccinimide) | |
| Cd$^{++}$ as Cd (NO$_3$)$_2$ | 1.5 grams per liter |
| Succinimide | 45.0 grams per liter |
| Potassium nitrate | 7.0 grams per liter |
| Ethylene diamine | 2 milliliters per liter |
| pH adjusted with potassium hydroxide to 9.5 | |
| Temperature | 20° C. (68° F.) |

-continued

| | |
|---|---|
| Current density | 1.0 A . dm$^{-2}$ (10 ASF) |
| Plating time | 10 minutes |
| Deposit | 98% Ag, 2% Cd-mirror-bright |
| Current efficiency | 98% |

EXAMPLE 25

| | |
|---|---|
| Potassium silver disuccinimide | 23.0 grams per liter |
| Cd$^{++}$ as cadmium acetate | 2.0 grams per liter |
| Succinimide | 65.0 grams per liter |
| Potassium acetate | 20.0 grams per liter |
| pH adjusted with potassium hydroxide to 9.0 | |
| Temperature | 20° C. (68° F.) |
| Current density | 1.5A . dm$^{-2}$ (15 ASF) |
| Plating time | 10 minutes |
| Deposit | 97% Ag, 3% Cd-mirror-bright |

EXAMPLE 26

| | |
|---|---|
| Ag as silver succinimide complex (Potassium silver disuccinimide) | 23.0 grams per liter |
| Au$^{+++}$ as HAuCl$_4$ | 1.2 grams per liter |
| Succinimide | 30.0 grams per liter |
| Potassium citrate | 25.0 grams per liter |
| Triethylene tetramine | 2.0 mls per liter |
| pH adjusted with potassium hydroxide to 8.7 | |
| Temperature | 25° C. (77° F.) |
| Current density | 2.0A . dm$^{-2}$ (20 ASF) |
| Plating time | 10 minutes |
| Deposit | 97.5% Ag, 2.5% Au-bright |

EXAMPLE 27

| | |
|---|---|
| Potassium silver disuccinimide | 23.0 grams per liter |
| Sb$^{+++}$ as antimony tartrate | 2.0 grams per liter |
| Succinimide | 65.0 grams per liter |
| Triethanolamine | 5 milliliters per liter |
| pH adjusted with potassium hydroxide to 12.5 | |
| Temperature | 25° C. (77° F.) |
| Current density | 1.5A . dm$^{-2}$ (15 ASF) |
| Plating time | 10 minutes |
| Deposit | 97% Ag, 3% Sb-dark bright |
| Current efficiency | 90% |

EXAMPLE 28

| | |
|---|---|
| Sodium silver disuccinimide | 23.0 grams per liter |
| Pd as Palladium ethylene diamine Sulfate | 4.0 grams per liter |
| Succinimide | 65.0 grams per liter |
| pH adjusted with sodium hydroxide to 8.0 | |
| Temperature | 25° C. (77° F.) |
| Current density | 1.0A . dm$^{-2}$ (10 ASF) |
| Plating time | 10 minutes |
| Deposit | bright |
| Current efficiency | 95% |

EXAMPLE 29

| | |
|---|---|
| Potassium silver disuccinimide | 20 grams per liter |
| Cd$^{+++}$ as Cd (NO$_3$)$_2$ | 23 grams per liter |
| Succinimide | 120 grams per liter |
| Potassium nitrite | 37 grams per liter |

-continued

| | |
|---|---|
| pH adjusted with potassium hydroxide to 8.5 | |
| Temperature | 25° C. (77° F.) |
| Current density | 1.0A . dm$^{-2}$ (10 ASF) |
| Plating time | 10 minutes |
| Deposit | 96.2% Ag, 3.8% Cd - mirror-bright |

EXAMPLE 30

| | |
|---|---|
| Potassium silver disuccinimide | 23 grams per liter |
| Cu$^{++}$ as Cu (NO$_3$)$_2$ . 3H$_2$O | 23 grams per liter |
| Succinimide | 120 grams per liter |
| Potassium nitrite | 37 grams per liter |
| pH adjusted with potassium hydroxide to 8.5 | |
| Temperature | 25° C. (77° F.) |
| Current density | 1.0A . dm$^{-2}$ (10 ASF) |
| Plating time | 10 minutes |
| Deposit | 98.3% Ag, 1.7% Cu - bright |
| Current efficiency | 20% |

EXAMPLE 31

| | |
|---|---|
| Potassium silver disuccinimide | 23 grams per liter |
| Cu$^{++}$ as Cu (NC$_3$)$_2$ . 3H$_2$ | 30 grams per liter |
| Succinimide | 150 grams per liter |
| Potassium nitrite | 37 grams per liter |
| pH adjusted with potassium hydroxide to 8.5 | |
| Temperature | 25° C. (77° F.) |
| Current density | 4A . dm$^{-2}$ (40ASF) |
| Plating time | 10 minutes |
| Deposit | 85.0% Ag, 15% Cu-bright |

EXAMPLE 33

| | |
|---|---|
| Potassium silver disuccinimide | 23 grams per liter |
| Au$^{+++}$ as HAuCl$_4$ | 20 grams per liter |
| Succinimide | 140 grams per liter |
| pH adjusted with potassium hydroxide to 10.0 | |
| Temperature | 30° C. (86° F.) |
| Current density | 1.0A . dm$^{-2}$(10 ASF) |
| Plating time | 10 minutes |
| Deposit | 99.5% Ag, 0.5% Au - semi-bright |

EXAMPLE 34

| | |
|---|---|
| Ammonium silver dimaleimide | 15 grams per liter |
| Maleimide | 36 grams per liter |
| pH - adjusted with NH$_4$OH | 10.0 |
| Temperature | 20° C. |
| Current density | 1.0A/dm$^2$ |
| Plating time | 5 minutes |
| Deposit | Silver - semi-bright to dull |

EXAMPLE 35

| | |
|---|---|
| Potassium silver disuccinimide | 25 grams per liter |
| Pd$^{++}$ as Palladium ethylene diamine sulfate | 16 grams per liter |
| Succinimide | 260 grams per liter |
| pH adjusted with potassium hydroxide to 9.0 | |

| | |
|---|---|
| Temperature | 25° C. (77° F.) |
| Current density | 1.0A . dm$^{-2}$ (10 ASF) |
| Plating time | 10 minutes |
| Deposit | Semi-bright |

In the preceding examples there is shown how to deposit silver and silver alloy electroplates from a noncyanide complex. This can be done, as indicated herein, with or without the polyamine, polyimine or metallic brighteners. Coloring and brightening of the silver plate can be achieved by alloying with co-plated metals in an amount from a few parts per thousand to about 5% of alloyed deposit as also described elsewhere herein.

As can be seen from the foregoing examples, a silver alloy plate can be prepared from the succinimide plating bath with very satisfactory results over a good range of concentrations, temperatures, and pH.

It will be evident that the terms and expressions that have been employed are used as terms of description and not of limitation. There is no intention in the use of these terms and expressions of excluding equivalents of the features shown and described or portions thereof and it is recognized that various modifications are possible within the scope of the invention claimed.

What is claimed is:

1. A water-soluble silver complex of the formulae:

wherein M is an alkali metal cation or ammonium, R is, in its instances of occurrence, the same or different, and is hydrogen or an alkyl or alkoxy moiety;

wherein R' is, in its instances of occurrence, the same or different, and is hydrogen or an alkyl moiety; or wherein each of M, R and R' is as characterized hereinabove.

2. A water-soluble silver complex as claimed in claim 1, wherein said complex is a pyrrolidine-2,5-dione-containing complex; and any alkyl or alkoxy moieties present therein contain from 1 to 4 carbon atoms.

3. A water-souble silver complex as claimed in claim 1, wherein said complex is a 3-pyrroline-2,5-dione containing complex, and any alkyl moieties present therein contain from 1 to 4 carbon atoms.

4. A water-soluble silver complex as claimed in claim 3, wherein said complex is an alkali metal, or ammonium, silver dimaleimide.

5. A water-soluble silver complex as claimed in claim 4, wherein said complex is potassium silver dimaleimide.

6. A water-soluble silver complex as claimed in claim 4, wherein said complex is an ammonium silver dimaleimide.

7. A water-soluble silver complex as claimed in claim 2, wherein said complex is an alkali metal or ammonium silver disuccinimide.

8. A water-soluble silver complex as claimed in claim 7, wherein said complex is potassium silver disuccinimide.

9. A water-soluble silver complex as claimed in claim 7, wherein said complex is ammonium silver disuccinimide.

10. The process that comprises reacting 2 moles of a water-insoluble silver pyrrolidine-2,5-dione complex of the general formula:

or a water-insoluble silver 3-pyrroline-2,5-dione complex of the general formula:

wherein R is, in its instances of occurrence, the same or different, and is hydrogen, or an alkyl or alkoxy moiety; and R' is, in its instances of occurrence, the same or different, and is hydrogen or an alkyl moiety with one mole equivalent of a reactant cation comprising an alkali metal cation or ammonium, to form respectively a water-soluble silver complex of the general formula:

, or

-continued wherein M is an alkali metal cation or ammonium corresponding to the reactant cation incorporated in the reaction and each of R and R' have the value assigned hereinabove.

11. A process as claimed in claim 10 wherein said water-insoluble silver complex is silver succinimide; said alkali metal cation is potassium; and said water-soluble silver complex is potassium silver disuccinimide.

12. The process that comprises contacting one mole of a water-insoluble silver pyrrolidine-2,5-dione complex of the general formula (I):

(I)

or a water-insoluble silver 3-pyrroline-2,5-dione complex of the general formula (II):

(II)

wherein R is, in its instance of occurrence, the same or different, and is hydrogen, or an alkyl or alkoxy moiety; and R' is, in its instances of occurrence, the same or different, and is hydrogen, or an alkyl moiety with at least one mole equivalent of a pyrrolidine-2,5-dione of the general formula (III):

(III)

wherein R is as defined above; or a 3-pyrroline-2,5-dione of the formula:

(IV)

wherein R' is as defined above; with a base containing an alkali metal or ammonium cation to form a corresponding water-soluble silver complex.

13. A process as claimed in claim 12, wherein one mole of said water-insoluble silver pyrrolidine-2,5-dione complex is contacted with at least one mole of said pyrrolidine-2,5-dione and wherein said base contains a sodium, potassium or ammonium cation.

14. A process as claimed in claim 12 wherein said water-insoluble silver pyrrolidine-2,5-dione complex is silver succinimide and said pyrrolidine-2,5-dione is succinimide and said cation is potassium.

15. A process as claimed in claim 12 wherein one mole of said water-insoluble silver 3-pyrroline-2,5-dione is contacted with at least one mole of said 3-pyrroline-2,5-dione and wherein said base contains a sodium, potassium or ammonium cation.

16. A process as claimed in claim 12 wherein said water-insoluble silver 3-pyrroline-2,5-dione is maleimide and said cation is potassium.

17. An aqueous, cyanide-free, electroplating bath for the electrodeposition of silver and silver alloys comprising an aqueous solution having a pH of 6 to 14 and incorporating a water-soluble silver complex of the general formula:

or the general formula:

or mixtures thereof; and where, in the foregoing formulae, M is an alkali-metal cation or ammonium, R is, in its instances of occurence, the same or different, and is hydrogen or an alkyl or alkoxy moiety, and R' is, in its instances of occurrence, the same or different, and is hydrogen or an alkyl moiety.

18. An aqueous, cyanide-free, electroplating bath for the electrodeposition of silver and silver alloys as claimed in claim 17 wherein said bath includes as a conductivity agent, a substituted or unsubstituted carboxylate of a monocarboxylic acid, dicarboxylic acid or tricarboxylic acid.

19. An electroplating bath as claimed in claim 18 wherein said carboxylate is citrate, acetate, maleate, succinate, malate, hydroxyacetate or mixtures thereof.

20. An aqueous, cyanide-free electroplating bath as claimed in claim 17, wherein there is incorporated, in addition to said silver complex, an alloying metal salt, wherein said alloying metal is gold, palladium or antimony or combinations thereof present in solution in an amount by weight of up to 50 grams per liter of solution as a coloring or hardening agent therefor.

21. An aqueous, cyanide-free electroplating bath as claimed in claim 20, wherein said alloying metal is gold.

22. An aqueous, cyanide-free electroplating bath as claimed in claim 20, wherein said alloying metal is antimony.

23. An aqueous, cyanide-free electroplating bath as claimed in claim 20, wherein said alloying metal is palladium.

24. An aqueous cyanide-free electroplating bath as claimed in claim 17, wherein said aqueous solution contains a brightener component, said brightener component being an amine of the formula:

or the cross-linked derivatives thereof; and wherein $R^2$ is hydrogen, amino or phenyl; each of $R^3$ and $R^4$ is hydrogen or an alkyl, aminoalkyl, or hydroxyalkyl, radical, or a radical of the formula:

where, in the foregoing formulae, any alkyl moiety included in $R^3$ and $R^4$ contains from 2 to 6 carbon atoms; and where each of $R^3$ and $R^4$ is a terminal radical; each such radical is an alkyl, aminoalkyl or hydroxyalkyl radical as defined hereinabove; m has a value of from 1 to 6; and each of x and y has a value of from 1 to a number sufficient, as the sum of x and y, to provide a polyalkylene polyamine having a molecular weight of up to 60,000.

25. An aqueous, cyanide-free electroplating bath as claimed in claim 24, wherein said amine is ethylene diamine.

26. An aqueous, cyanide-free electroplating bath as claimed in claim 24, wherein said amine is diethylene triamine.

27. An aqueous, cyanide-free electroplating bath as claimed in claim 24, wherein said amine is triethylene tetramine.

28. An aqueous, cyanide-free electroplating bath as claimed in claim 24, wherein said amine is benzyl amine.

29. In a process for the electrodeposition of silver and silver alloys by passing an electric current to a cathode to be plated, the improvement that comprises passing said current through an electroplating bath including an aqueous solution having a pH of 6 to 14 and a water-soluble silver complex of the general formula:

or the general formula:

or mixtures thereof; and where, in the foregoing general formulae, M is an alkali metal cation or ammonium, R is, in its instances of occurrence, the same or different, and is hydrogen or an alkyl or alkoxy moiety, and R' is, in its instances of occurrence, the same or different, and is hydrogen or an alkyl moiety, and wherein said process is carried out at a temperature within the range of 20° C. to 40° C.

30. A process as claimed in claim 29, wherein the cathodic current density is from 0.1 A per square decimeter to 3.0 A per square decimeter.

* * * * *

UNITED STATES PATENT OFFICE
CERTIFICATE OF CORRECTION

Patent No. 4,246,077        Dated  July 28, 1981

Inventor(s) Edward Hradil et al.

It is certified that error appears in the above-identified patent and that said Letters Patent are hereby corrected as shown below:

Col. 4, line 31,   after "in" and before "at least" insert --which--.

Col. 4, line 32,   cancel "is" and substitute --are--.

Col. 5, line 4,    cancel "(21)" and substitute --2--.

Col. 16, line 27,  cancel "$Cu(NC_3)_2 \cdot 3H_2$" and substitute --$Cu(NO_3)_2 \cdot 3H_2O$--.

Signed and Sealed this

*Twenty-seventh* Day of *October 1981*

[SEAL]

Attest:

GERALD J. MOSSINGHOFF

*Attesting Officer*   Commissioner of Patents and Trademarks